(12) United States Patent
Tepic et al.

(10) Patent No.: US 10,299,907 B2
(45) Date of Patent: May 28, 2019

(54) PROSTHETIC SYSTEM FOR ORTHOPEDIC REPAIR

(75) Inventors: Slobodan Tepic, Zurich (CH); Randy Acker, Ketchum, ID (US); Kent Harrington, Brookline, MA (US); Daniela Hitz, Wettswil (CH); Daniel Martin, Palo Alto, CA (US); Phillips B. Stearns, South Hamilton, MA (US)

(73) Assignee: Kyon AG, Zurich (CH)

( * ) Notice: Subject to any disclaimer, the term of this patent is extended or adjusted under 35 U.S.C. 154(b) by 0 days.

(21) Appl. No.: 14/112,041

(22) PCT Filed: Apr. 16, 2012

(86) PCT No.: PCT/US2012/033845
§ 371 (c)(1),
(2), (4) Date: May 5, 2014

(87) PCT Pub. No.: WO2012/145275
PCT Pub. Date: Oct. 26, 2012

(65) Prior Publication Data
US 2014/0243977 A1 Aug. 28, 2014

Related U.S. Application Data

(60) Provisional application No. 61/476,262, filed on Apr. 16, 2011.

(51) Int. Cl.
*A61F 2/08* (2006.01)
(52) U.S. Cl.
CPC ..... *A61F 2/0811* (2013.01); *A61F 2002/0841* (2013.01); *A61F 2002/0852* (2013.01); *A61F 2002/0858* (2013.01); *A61F 2002/0864* (2013.01); *A61F 2002/0882* (2013.01)

(58) Field of Classification Search
CPC ... A61F 2002/0823; A61F 2/08–2/0811; A61F 2002/0817–2002/0888; A61F 2002/0864
See application file for complete search history.

(56) References Cited

U.S. PATENT DOCUMENTS

| 3,766,610 | A | 10/1973 | Thorsbakken |
| 4,510,934 | A | 4/1985 | Batra |
| 4,656,806 | A | 4/1987 | Leibhard et al. |
| 4,898,505 | A | 2/1990 | Froehlich |
| 5,336,240 | A | 8/1994 | Metzler et al. |
| 5,464,427 | A | 7/1995 | Curtis et al. |
| 5,480,403 | A | 1/1996 | Lee et al. |

(Continued)

FOREIGN PATENT DOCUMENTS

| EP | 2623066 | 8/2013 |
| FR | 2683715 | 11/1991 |

(Continued)

*Primary Examiner* — Brian E Pellegrino
(74) *Attorney, Agent, or Firm* — Occhiuti & Rohlicek LLP

(57) ABSTRACT

The present invention features systems for orthopedic repair of, for example, a joint. The present systems deviate from conventional systems by virtue of combining a finer prosthetic ligament with a robust anchor. The relationship between these components and their various features are described herein and result in joint reconstruction in human and veterinary settings that is less likely to fail over time.

22 Claims, 9 Drawing Sheets

(56) References Cited

U.S. PATENT DOCUMENTS

| | | | |
|---|---|---|---|
| 5,571,139 A | 11/1996 | Jenkins, Jr. | |
| 5,575,819 A * | 11/1996 | Amis | A61F 2/08 623/13.13 |
| 5,702,397 A | 12/1997 | Goble et al. | |
| 5,707,395 A | 1/1998 | Li | |
| 5,720,753 A | 2/1998 | Sander et al. | |
| 5,891,146 A * | 4/1999 | Simon | A61B 17/863 411/414 |
| 5,911,721 A | 6/1999 | Nicholson | |
| 5,935,129 A | 8/1999 | Mcdevitt | |
| 5,957,953 A | 9/1999 | Dipoto et al. | |
| 5,989,253 A | 11/1999 | Bigliardi | |
| 6,086,608 A | 7/2000 | Ek et al. | |
| 6,350,126 B1 | 2/2002 | Levisman | |
| 6,436,142 B1 | 8/2002 | Paes et al. | |
| 6,527,794 B1 | 3/2003 | McDevitt et al. | |
| 6,575,987 B2 | 6/2003 | Gellman et al. | |
| 6,585,730 B1 | 7/2003 | Foerster | |
| 6,616,694 B1 | 9/2003 | Hart | |
| 6,656,185 B2 | 12/2003 | Gleason et al. | |
| 6,923,824 B2 | 8/2005 | Morgan et al. | |
| 7,083,638 B2 | 8/2006 | Foerster | |
| 7,090,690 B2 | 8/2006 | Foerster et al. | |
| 7,147,652 B2 | 12/2006 | Bonutti et al. | |
| 7,172,595 B1 | 2/2007 | Goble | |
| 7,217,279 B2 | 5/2007 | Reese | |
| 7,491,217 B1 | 2/2009 | Hendren et al. | |
| 7,828,820 B2 | 11/2010 | Stone et al. | |
| 7,976,565 B1 | 7/2011 | Meridew | |
| 8,133,258 B2 | 3/2012 | Foerster et al. | |
| 8,361,113 B2 * | 1/2013 | Stone | A61B 17/0401 606/213 |
| 8,454,654 B2 | 6/2013 | Ferragamo et al. | |
| 8,523,902 B2 | 9/2013 | Heaven et al. | |
| 2003/0004545 A1 | 1/2003 | Burkart et al. | |
| 2003/0195563 A1 | 10/2003 | Foerster | |
| 2004/0127907 A1 | 7/2004 | Dakin et al. | |
| 2004/0267360 A1 | 12/2004 | Huber | |
| 2005/0159812 A1 * | 7/2005 | Dinger, III | A61F 2/0811 623/13.14 |
| 2005/0209639 A1 | 9/2005 | Gidwani et al. | |
| 2005/0216058 A1 | 9/2005 | Egan et al. | |
| 2005/0288762 A1 | 12/2005 | Henderson et al. | |
| 2006/0116685 A1 | 6/2006 | Urbanski et al. | |
| 2006/0135996 A1 | 6/2006 | Schwartz et al. | |
| 2006/0149258 A1 | 7/2006 | Sousa | |
| 2006/0235413 A1 | 10/2006 | Denham et al. | |
| 2006/0247642 A1 | 11/2006 | Stone et al. | |
| 2006/0265010 A1 | 11/2006 | Paraschac et al. | |
| 2007/0038221 A1 | 2/2007 | Fine et al. | |
| 2007/0118217 A1 | 5/2007 | Brulez et al. | |
| 2007/0203498 A1 | 8/2007 | Gelber et al. | |
| 2007/0225719 A1 | 9/2007 | Stone et al. | |
| 2008/0234758 A1 | 9/2008 | Fisher et al. | |
| 2008/0249567 A1 | 10/2008 | Kaplan | |
| 2008/0288070 A1 | 11/2008 | Lo | |
| 2009/0012522 A1 | 1/2009 | Lob | |
| 2009/0234451 A1 * | 9/2009 | Manderson | A61B 17/8645 623/13.14 |
| 2009/0292321 A1 | 11/2009 | Collette | |
| 2010/0318188 A1 | 12/2010 | Linares | |
| 2011/0046733 A1 | 2/2011 | Eggli | |
| 2011/0066185 A1 | 3/2011 | Wotton, III | |

FOREIGN PATENT DOCUMENTS

| | | |
|---|---|---|
| GB | 2084468 | 4/1985 |
| WO | WO93/21857 | 11/1993 |
| WO | WO 95/00318 | 1/1995 |
| WO | WO95/15726 | 6/1995 |
| WO | WO 97/00766 | 1/1997 |
| WO | WO 02/17795 | 3/2002 |
| WO | WO2007/147634 | 12/2007 |
| WO | WO 2008/131370 | 10/2008 |
| WO | WO 2010/123835 | 10/2010 |
| WO | WO/2012/145275 | 10/2012 |

* cited by examiner

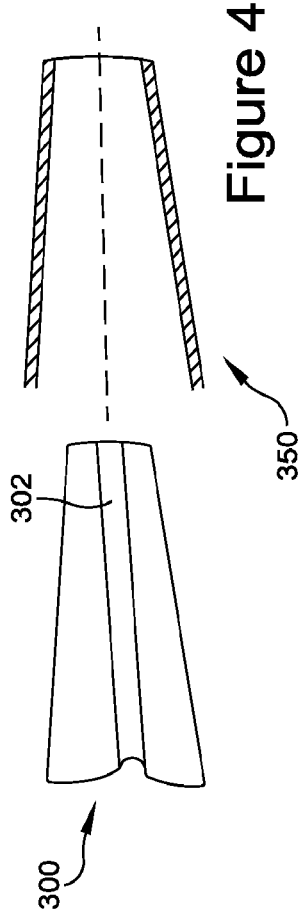
Figure 4a
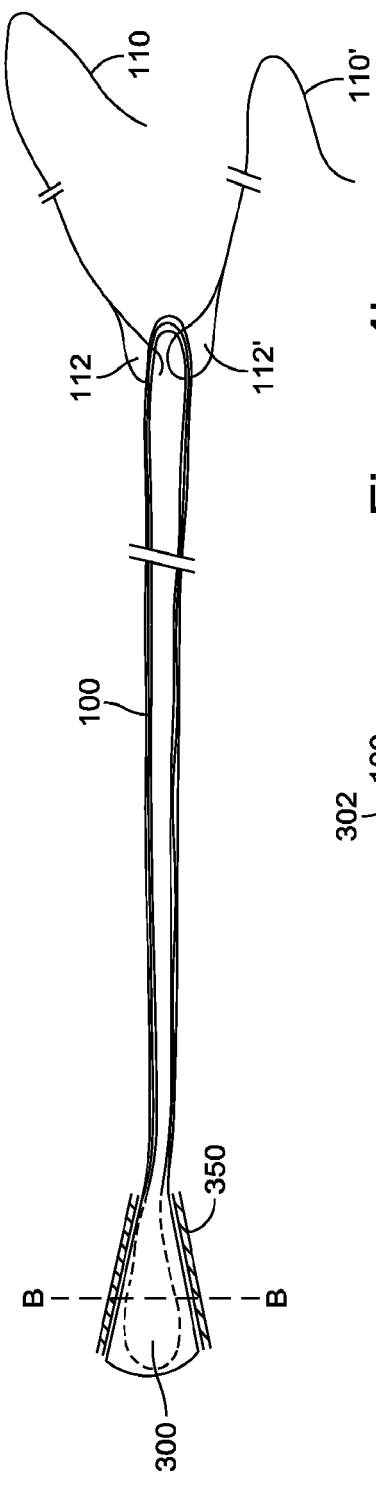
Figure 4b
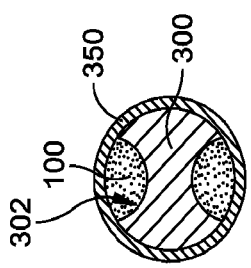
Section B-B

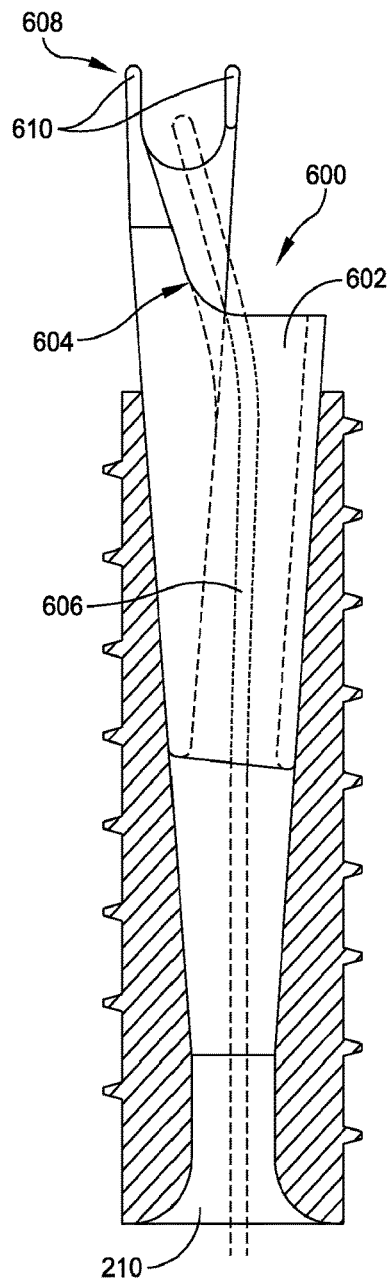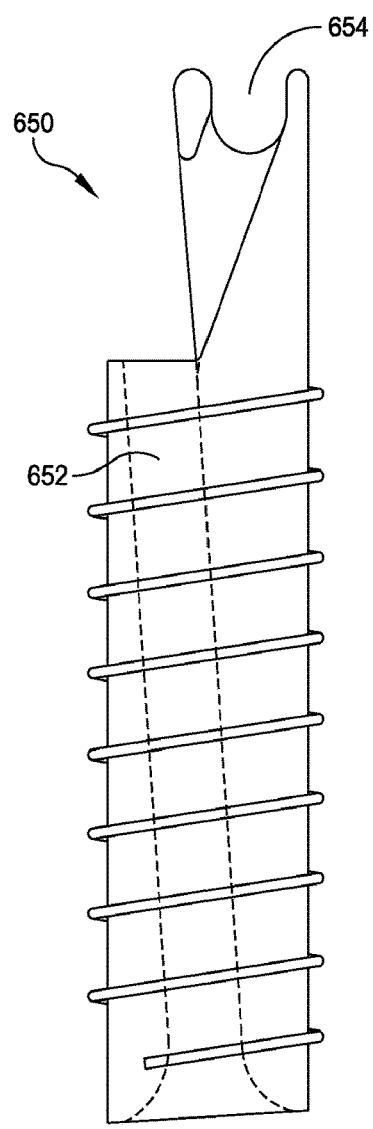
Figure 7a
Figure 7b

PROSTHETIC SYSTEM FOR ORTHOPEDIC REPAIR

CROSS-REFERENCE TO RELATED APPLICATIONS

This application is a U.S. national phase application of the international application PCT/US2012/033845, filed Apr. 16, 2012, which claims the benefit of the filing date of U.S. Application No. 61/476,262, filed Apr. 16, 2011. The content of the earlier-filed applications is hereby incorporated by reference herein in its entirety.

FIELD OF THE INVENTION

The present invention relates to a repair or prosthetic system useful in orthopedic surgeries (e.g., to repair or reconstruct the anterior cruciate ligament (ACL)). The system comprises uniquely configured anchors and prosthetic ligaments.

BACKGROUND

The Anterior Cruciate Ligament (ACL) in the human knee joint, commonly called the Cranial Cruciate Ligament in the canine stifle, is frequently torn in trauma or, as it happens in dogs, fails after a degenerative process of still unknown etiology. Direct repair is usually not possible; when attempted, it predictably fails.

In human orthopedics, the standard protocol calls for replacement by an autograft or an allograft, a part of the patellar ligament, or other tendons harvested for this purpose. The procedure results in a stable knee, but the long term performance is often unsatisfactory with over half of the cases resulting in arthrosis of the joint. There is also unwanted variability associated with the autograft and allograft tendons. Such natural tissue graft placement does not truly reproduce the function of the original ACL, as the grafts cannot perfectly imitate the anatomy of the original ACL.

In dogs, the standard procedure is either an extracapsular suture (usually placed on the lateral side of the joint) that approximates the function of the ligament or one of the geometry modifying surgical techniques (e.g. tibial plateau leveling osteotomy (TPLO), cranial closing wedge osteotomy (CWO), or tibial tuberosity advancement (TTA)). Intra-articular prostheses are also occasionally used, but those have generally failed. Extracapsular sutures also fail.

The canine techniques described above are in many cases intended to provide stability of the joint for several weeks while waiting for fibrosis to develop around the joint, which should then provide for long term stability. However, arthrosis of the joint is the rule rather than the exception within about one year. A variety of anchors have been used to fix the ends of an ACL reconstruction into bones. Most commonly, the anchors are so-called interference screws, which are designed to be inserted alongside the ligament replacement (e.g., a transplanted tendon or ligament or an artificial ligament) within an anchor hole or tunnel that is drilled into the bone. The interference screw jams the ligament replacement against the bone within the anchor hole. FIG. 1 shows an ACL bone anchor 1 of the interference screw type inserted, into a bone 3 in a direction 5 that jams the prosthetic tissue 2 within the hole 4 in order to resist a pull-out force 6. Such screws are made either from metal, most commonly titanium, or bioresorbable polymers.

In another commonly used technique, a so-called cross-pin technique, a loop of the prosthesis is anchored within a hole drilled in the femoral condyle. In all cases, the prosthesis exits the tunnel by bending over the edge of the bone. Healing and remodeling of the bone are expected to fill the gaps and to result in a natural-like anchorage of the prosthesis in the bone. FIG. 2 shows an ACL anchor 7 of the transverse, or cross-pin type, inserted into the bone of the femoral condyle 12 through a hole 10. A front section 8 of the anchor 7 passes through a loop of a prosthesis 9 inserted through the hole 11. In this manner, the prosthesis can support the pull 13 exerted on it in use.

Neither of these techniques is suitable for a permanent anchorage of an artificial material ACL replacement. Bending the prosthesis over the edge of a hole will lead to both bone loss due to contact resorption and mechanical damage of the ligament. Ultimately, the reconstruction fails due to bending fatigue and wear of the ligament and loss of bone at the edge of the hole.

An alternative method of using screw anchors with the prosthesis fixed in their central, axial hole also does not provide for a durable anchorage, because in all of the designs of which we are aware, the bending of the prosthesis over the edge of the hole exceeds the fatigue and abrasion limits of even the best materials.

SUMMARY

Described herein are unconventional systems for orthopedic repair. In one aspect, the invention features a prosthetic system for surgical repair of a joint that includes a first anchor, a second anchor, a prosthetic ligament, and a restraint for the prosthetic ligament. The first anchor includes an elongated body defining a longitudinal tunnel that connects a leading end of the first anchor with a trailing end of the first anchor; the leading end of the first anchor has a cross-sectional diameter that is no greater than the cross-sectional diameter of the elongated body of the first anchor (e.g., excluding the major diameter of the threads); the prosthetic ligament is dimensioned to bridge a gap between the first anchor and the second anchor; and the restraint is either an integral part of the trailing end of the first anchor or configured to conform thereto.

The elongated body can include an outer surface at least partially covered by threads and can be fashioned from a non-resorbable material (e.g., stainless steel, titanium, a titanium alloy, a zirconium alloy, a ceramic, or an alloy of chromium and cobalt). A portion of the trailing end can be shaped to engage an insertion tool (e.g., the portion of the trailing end that engages the insertion tool can be non-circular (e.g., polygonal) or circular in cross-section). The portion of the trailing end that engages the insertion tool (e.g., an internal surface) can also be tapered (e.g., conical). The portion of the trailing end that engages the insertion tool can be a portion of the external surface of the trailing end (e.g., an indentation or groove).

Where the restraint is an integral part of the trailing end of the first anchor, it can be (or can include) a hook or bar extending from the trailing end of the first anchor. Where the restraint is separable from the trailing end of the first anchor, it can be (or can include) a dowel, in which case the trailing end of the first anchor can include a recess (e.g., a conical recess) configured to receive the dowel. To secure the prosthetic ligament, the restraint (e.g., a dowel) can include a longitudinal channel through which the prosthetic ligament can pass, defining the pathway of the ligament in the channel. The longitudinal channel can be formed on an internal surface of the dowel. Where the longitudinal channel is external, the restraint may have a pair of channels formed on an external surface and the devices may further include a sleeve (e.g., a dowel sleeve of, for example, polyether ether ketone) positioned between the restraint and the conical recess of the trailing end of the first anchor.

The leading end of the first anchor can include a curved exit, which can be integral to the leading end of the first anchor or formed by means of including an eyelet (a separate eyelet) surrounding the longitudinal tunnel at the leading end of the anchor. The surface of the curved exit can be a hard, low friction, low roughness, and/or low abrasion surface having a roughness ($R_a$), for example, of less than about 0.5 μm. The surface can be or can include a ceramic (e.g., an amorphous diamond-like coating (ADLC)) or an oxidized metal (e.g., zirconium oxide or aluminum oxide). The surface can be ion implanted, diffusion hardened, oxidized, or treated using an ion beam assisted deposition process.

The prosthetic ligament can include a plurality of fibers that are aligned substantially parallel to one another. In some embodiments, the fibers are intermingled (e.g., twisted), and the intermingled fibers can be braided, further twisted, or braided and twisted. The fibers can have diameters in the range of about 10 to 20 μm and can be formed from a high strength, high modulus polymer (e.g., a polymer of polyethylene). The curved exit of the anchor can have a radius of curvature that is at least or about 50-100 times larger than the diameter of a fiber in the prosthetic ligament. For example, the radius of curvature can be at least or about 1 mm, and the diameter of a fiber in the prosthetic ligament can be about 10 μm. The curved exit can have a radius of curvature of at least $(k/2)(d/\varepsilon_{max})$, wherein d is the diameter of individual fibers in the prosthetic ligament, $\varepsilon_{max}$ is the allowed strain in fatigue of the fibers' material, and k is a factor between 1 and 4 (e.g., 1-2 or 2-3) allowing for strain associated with suture tension in cyclic use.

The first anchor and the second anchor can be substantially identical and in any embodiment, the system can further include a passing lead (e.g., a pair of passing leads) that is secured around the prosthetic ligament and configured to facilitate passage of the prosthetic ligament from the leading end of the first anchor, across the gap between the first anchor and the second anchor, and through the second anchor.

The elongated body of the anchor can define a pair of longitudinal tunnels that connect a leading end of the first anchor with a trailing end of the first anchor.

In another aspect, the invention features an assembled prosthetic ligament comprising a prosthetic ligament, a supplemental restraint, and a passing lead, wherein the prosthetic ligament is confined at a first end by the supplemental restraint and captured at a second end by the passing lead.

In another aspect, the invention features kits including one or more of the component parts described herein. For example, a kit can include a first anchor, a prosthetic ligament, a restraint for the prosthetic ligament (where the restraint is not integral to the anchor), and instructions for use. The kit can further include a second anchor. The kit can include an assembled prosthetic ligament. The kit can include a threader and, optionally, a threader stop. The kit can include a plurality of prosthetic ligaments of varying length. The kit can include an insertion tool. The kit can include two or more of any component part described herein (e.g., a second or third restraint of the same or differing types). For example, in one embodiment, the invention features a kit that includes an assembled prosthetic ligament and instructions for use, wherein the prepared prosthetic ligament comprises a prosthetic ligament, a supplemental restraint, and a passing lead, wherein the prosthetic ligament is confined at a first end by the supplemental restraint and captured at a second end by the passing lead. In any of the kits including a prosthetic ligament, the ligament can be confined at one end by a pair of passing leads. In, any of the kits, one can include one or more of the following: instructions for use; a first anchor, a second anchor, a restraint for placement on the trailing end of the second anchor, an insertion tool, a threader, and, optionally, a threader stop.

In another aspect, the invention features methods of surgically repairing a joint. The methods can be carried out by deploying a prosthetic system as described herein in a patient in need of treatment. While use with human patients is certainly expected, the invention is not so limited and encompasses veterinary use as well. Thus, the patient can be a human being or a canine, feline, or equine animal. Where the patient is a human being, the joint subject to repair can be a shoulder, elbow, wrist, hip, knee, or ankle joint. Where the patient is non-human, the joint subject to repair can be a should, elbow, wrist, hip, knee, or ankle joint, or the equivalent thereof in the species being treated. The methods of the invention can further include the steps of: (a) providing a bone hole in each of two opposing bones, (b) placing, in each bone hole, an anchor, and (c) passing the prosthetic ligament (i) through a first anchor, from the trailing end of the first anchor to the leading end of the first anchor, (ii) across the gap between the two opposing bones, and (iii) through the second anchor, from the leading end of the second anchor to the trailing end of the second anchor. The methods of the invention can further include the steps of: (d) securing the prosthetic ligament in the trailing end of the second anchor.

While the invention is not limited to prostheses that achieve success through any particular physiological mechanism, we do expect to see osseointegration between the bone and the anchor, and outcomes may be improved by providing an interface between the hard anchor material and the softer prosthesis. The ligament prosthesis itself is preferably strong, abrasion resistant, and relatively small (allowing for room at the curved exit of the hard anchor and a more well defined isometric point of origin). We expect the size disparity between the diameter of the bone hole and the diameter of the ligament prosthesis to provide certain advantages. This disparity is discussed at length further below. Among the advantages of the present prostheses may be one or more of: improved durability, affordability, simplicity, reliability, and predictability. A priority for the inventors has been to provide an adequate radius of curvature at the curved exit of the anchor and to adjust this radius with respect to the specific fatigue properties of the prosthetic ligament fibers and the diameter of those fibers. Unlike orthopedic repair systems known in the art, the present system does not try to fit the ligament prosthesis snugly into a bone tunnel. This feature allows for easier replacement of the prosthetic ligament should that prove necessary. Further, the present system does not try to necessarily maximize the ligament prosthesis diameter with respect to the diameter of the bone hole nor to approximate the size of the natural ligament being replaced. Instead, the present systems feature a disparity between the size of the bone hole and the diameter of the prosthesis and fibers therein, predicated on the radius of curvature of the anchor at the curved exit. Some advantages may be conferred by the large outer surface area of the anchor relative to the surface area of the longitudinal tunnel through the anchor. This relationship provides adequate surface area for load transfer from the strong ligament to the relatively weaker cancellous bone. The present systems represent a different approach to orthopedic repair. While we are not attributing any particular advantage to any particular feature of the present systems, we note the inclusion in the present systems of high performance polymeric fibers and configurations in which those fibers bear certain relationships to an anchor as described herein.

BRIEF DESCRIPTION OF THE DRAWINGS

FIG. 4 shows components of the prosthetic system according to the present invention.

FIG. 7 shows a separable restraint (a dowel) with a restraining pathway for the ligament.

DETAILED DESCRIPTION

The present invention relates to a prosthetic system useful in orthopedic surgeries (e.g., to repair the anterior cruciate ligament (ACL)); to component parts thereof; to the system or to component parts thereof as packaged for distribution or sale (e.g., as a kit); and to methods of joint repair.

Referring to FIG. 3, selected components of the prosthetic system are illustrated. FIGS. 3a-3d illustrate a prosthetic ligament 100 which, due to its shape, we may also refer to as a prosthetic ligament loop. The prosthetic ligament 100 is formed by providing a number of fibers, which may be present as either individual fibers (i.e., as monofilaments) or in groups (e.g., in the form of a yarn). Multiple individual fibers or multiple groups of fibers (yarns) can be manufactured as contiguous loops that are aligned or stacked (FIG. 3a; by analogy, as a number of equally sized loops of the same rope could be aligned or stacked on top of one another, and the two free ends tied). Alternatively, multiple individual fibers or yarns can be manufactured as strands and aligned linearly before the plurality of the ends of the individual fibers or the individual yarns are brought together and tied. FIG. 3b illustrates a knot being tied between a first end and a second end of all of the individual and linearly aligned fibers or yarns of the prosthetic ligament 100. To facilitate the knot, the ends of the fibers or yarns can be capped 121, glued, or otherwise held together. For example, in one embodiment, a superficial net-like absorbable suture may be manufactured around the central bundle to contain it for easier handling (e.g., at the time of manufacture or surgery). Alternatively, a single individual fiber or a single group of fibers (e.g., a yarn) can be manufactured to a longer length and then looped around itself before one end of the long, single fiber is tied to the other end of the long, single fiber or one end of the long intermingled fiber is tied to the other end of the long fiber or group of fibers. The ends can be joined by splicing or tying a knot with the two ends of the single individual fiber or single yarn (FIG. 3c). We use the term "knot" to refer to any form of tangled engagement, and any engagement can be reinforced once made with an adhesive or other bonding agent. Strong entanglement may also be achieved with a jet of air.

Figure 1:
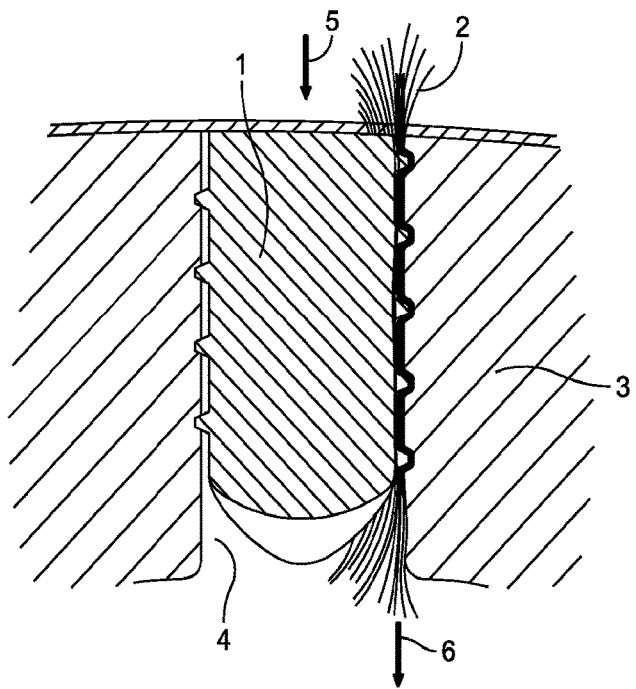
FIG. 1 is a cross-sectional view of a state of the art interference screw for anchoring a ligament replacement tissue within a bone tunnel. Conventionally, the ligament replacement fills as much of the bone hole as possible and is jammed in place by an interference screw. The ligament is shown here only partially to allow a clearer view of the body of the screw and the overall configuration.
Figure 2:
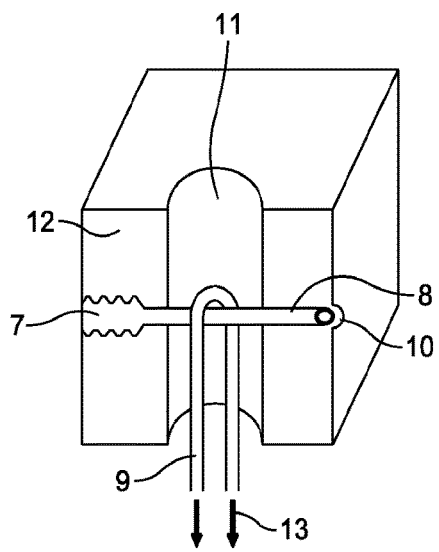
FIG. 2 is a cross-sectional view of a state of the art transverse pin for anchoring ACL replacement in the lateral condyle of the femur.
Figure 3A:
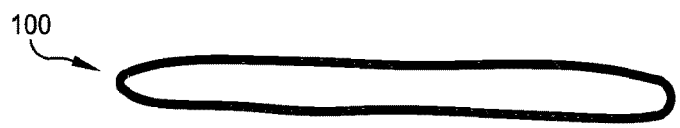
FIG. 3 shows components of the prosthetic system according to the present invention.
Figure 3B:
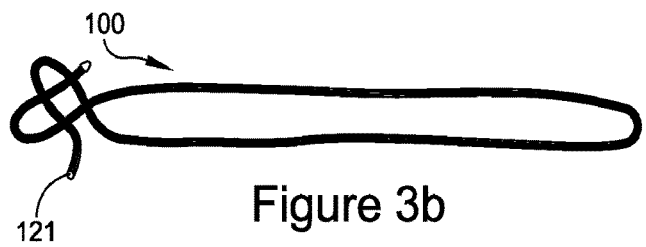
Figure 3C:

In another embodiment, the prosthetic ligament is formed using groups of fibers (e.g., yarns) that are themselves intermingled (e.g., braided or twisted). Thus, in terms of fine structure, the prosthetic ligament can include fibers (i.e., monofilaments) that are arranged roughly parallel to one another; fibers (i.e., monofilaments) that are grouped for example into yarns, that are arranged roughly parallel to one another; and fibers that are further related (e.g., gathered into yarns, braided, or twisted). The ends of individual fibers can be joined either singly or collectively; the ends of intermingled fibers can be joined (e.g., the ends of yarns can be joined) either singly or collectively; and the ends of fibers in more complex arrangements (e.g., the ends of intermingled yarns) can be joined either singly or collectively. As noted, the join can be achieved by a knot, adhesive, or both means. In prosthetic ligaments having a continuous loop of material (as shown in FIG. 3c), there may be more equal self-adjusting tension on the fibers.

Figure 3D:
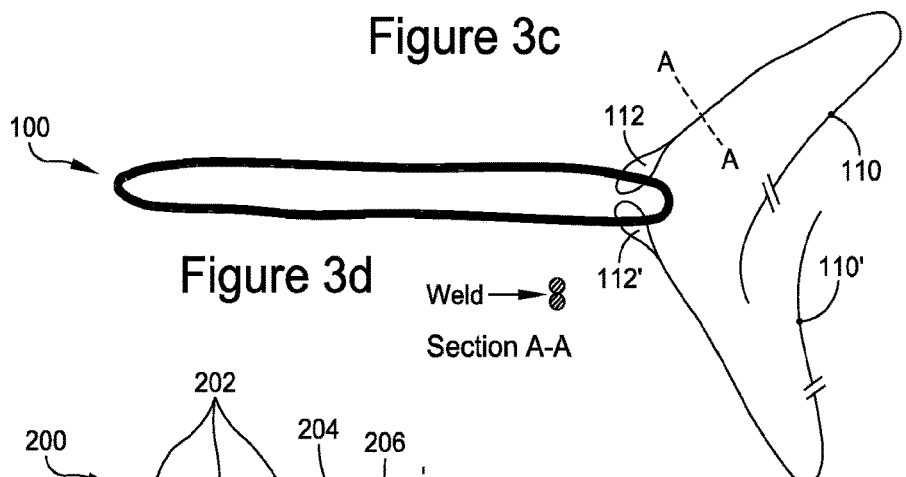
Figure 3E:
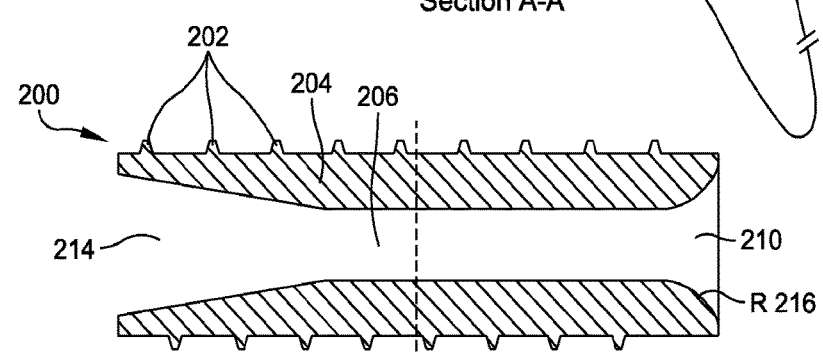

To facilitate deployment, the prosthetic ligament 100 can be temporarily captured by one or more passing leads 110 (FIG. 3d). The passing leads 110 and 110' can be formed by welding a length of a filament (e.g., a polymeric filament), as shown in section A-A of FIG. 3d, leaving the loops 112 and 112', respectively, enclosing the prosthetic ligament 100. Deployment of the prosthetic system, including the use of the passing leads, is described further below. An anchor 200 is used to fix the prosthetic ligament (FIG. 3e), and using first and second anchors allows fixation of the prosthetic ligament 100 between two bones. According to one embodiment of the invention, the external surface of at least a portion of the elongated body of the anchor comprises threads 202, the threads being preferably self-tapping. The surface of the anchor bearing the threads may also have a coating to enhance osseointegration, such as calcium phosphate or titanium (Spire Corporation). The elongated body 204 of the anchor defines a longitudinal tunnel 206, which may be drilled through the whole anchor and may be centered on the long axis of the anchor. We may refer to a centered tunnel as an axial tunnel. At the leading end 208 of the anchor, the longitudinal tunnel 206 broadens into a curved exit 210, with a radius of curvature 216, while at the trailing end 212 of the anchor, the longitudinal tunnel 206 broadens into a conical recess 214. Usually, the leading end of the anchor enters the bone first, and the trailing end trails behind. In the methods of the invention, the surgeon may insert both anchors from the "outside in" such that the leading ends roughly face one another from opposing sides of the joint. The surgeon, of course, has discretion in the direction of insertion of the anchors and may place them in some circumstances such that the trailing end of the anchor enters the articular side of the hole. The anchors of the present system can be configured such that neither the leading end nor the trailing end has a diameter in cross-section that is greater than the diameter of the elongated body in cross-section. For this purpose, the diameter of the elongated body excludes the major diameter of the threads and refers to the body at its core.

Figure 3F:
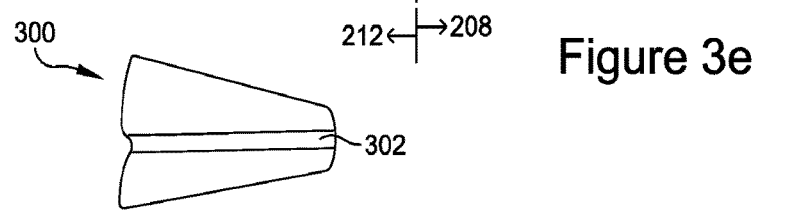

The prosthetic ligament can be held at both ends by restraints. More specifically, a first end of the prosthetic ligament can be held by a first restraint in the trailing end of a first anchor and a second end of the prosthetic ligament can be held by a second restraint in the trailing end of a second anchor. FIG. 3f illustrates a separable restraint (i.e., one that is not an integral part of the anchor) in the form of a conical dowel 300. The filaments of the prosthetic ligament 100 are held in a longitudinal channel 302 of the dowel 300. As discussed further below, the fibers of the prosthetic ligament may be further restrained and protected by a dowel sleeve. For added clarity, in one embodiment, the cone-shaped dowel 300 is suitably fashioned to be positioned within the conical recess 214 of the longitudinal tunnel 206 at the trailing end 212 of the anchor 200. The separable restraints, including the cone-shaped dowel 300 illustrated in FIG. 3f, can vary in length to allow for fine adjustment of the length of the prosthetic ligament 100 inserted into the joint. The surgeon may choose from restraints of several lengths, with the restraints varying from one another in about 1 to 2 mm increments. Generally, the restraints can have a length of about two to ten (e.g., 3-5) times the diameter of the anchor. When tapered, the angle of the taper can vary. For example, the dowel taper can vary from about four to fifteen degrees (e.g., about 4, 5, 8; or 10°).

Referring to FIG. 4, a dowel 300 may also be provided with a dowel sleeve 350 to protect the filaments of the ligament loop 100, which run within the longitudinal channel 302 of the dowel 300 from being damaged by surface-to-surface (e.g., metal-to-metal) contact between the separable restraint and the anchor (FIG. 4a). In one assembly, which we may refer to as an assembled prosthetic ligament, prosthetic ligament 100 is wrapped around a dowel 300 with the dowel sleeve 350 helping to secure the filaments of the prosthetic ligament 100 within the longitudinal channels 302 of the dowel 300 as shown in Section B-B (FIG. 4b). In this illustration, the dowel 300 includes two longitudinal channels 302 positioned essentially opposite one another. One of ordinary skill in the art will recognize that the longitudinal channels can be positioned at any distance apart as long as the prosthetic ligament remains secure around the restraint. Separable and integral restraints with a single longitudinal channel are discussed further below, as are restraint structures that are separable from the anchor or integrated with the anchor.

Figure 5A:
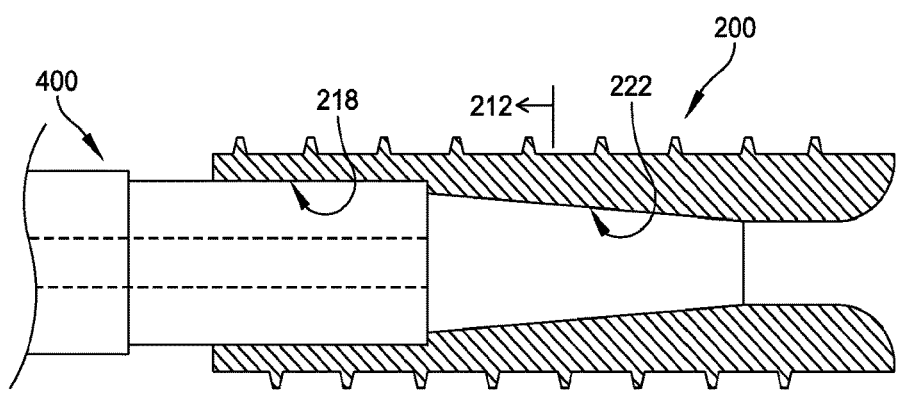
FIG. 5 shows various configurations for the insertion tool and trailing end of the anchor.
Figure 5B:
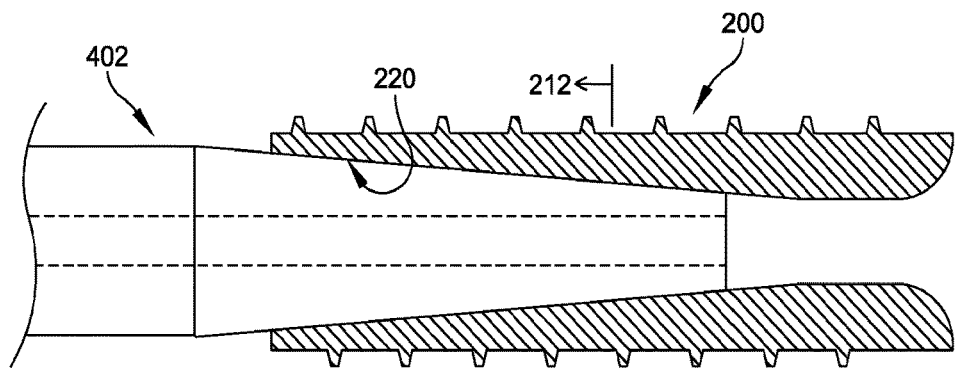
Figure 5C:
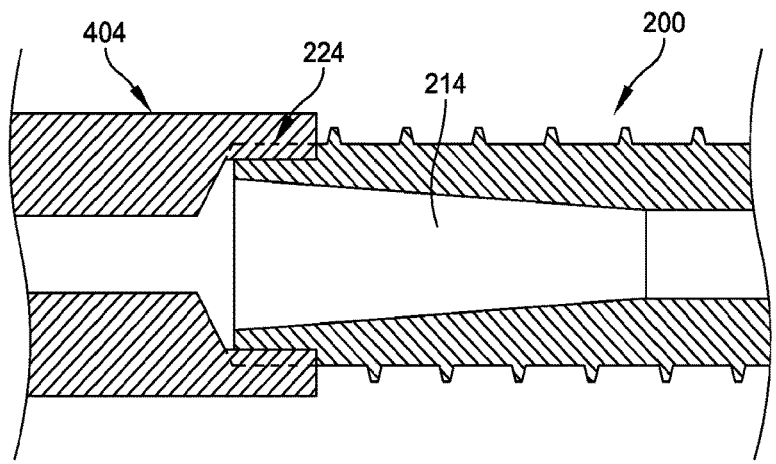

Referring to FIG. 5, these drawings illustrate insertion tools 400, 402, and 404 and various configurations for the trailing end 212 of an anchor 200 for accommodating the insertion tools. Generally, an insertion tool for driving an anchor into bone can be configured to engage with the trailing end 212 of an anchor 200 on either an internal surface of the anchor (as in FIGS. 5a and 5b) or an external surface of the anchor (as in FIG. 5c). In one embodiment, the recess in the trailing end 212 of the anchor 200 has a surface 218 that is non-conical and non-circular in cross-section for receiving an insertion tool 400 that is non-conical and non-circular in cross-section (FIG. 5a). In another embodiment, the recess in the trailing end 212 of the anchor 200 has a surface 220 that is conical and non-circular in cross-section. Generally, the recess in the terminal end of an anchor can be multi-functional and that functionality can be provided by either a single surface (as shown in FIG. 5b) or multiple surfaces (as shown in FIG. 5a). In FIG. 5a, one surface 218 is shaped to receive the insertion tool, and another surface 222 is shaped to receive a separable restraint. In FIG. 5b, one surface 220 receives both the insertion tool and the separable restraint. In this embodiment, both the insertion tool point 405 and the surface 220 are conical in shape (or "tapered" (although not all tapers are cones)) and are congruent. In any embodiment, the tip of the insertion tool and the portion of the anchor with which it engages can be fully congruous in shape. In FIG. 5c, the insertion tool 404 engages an external surface 224 of the anchor 200. The recess 214 is tapered and can be circular or non-circular in cross-section. Where the insertion tool engages with an external surface of the anchor, there is no necessity for congruence between the shape of the insertion tool and the internal surface of the anchor at its trailing end. For example, as shown in FIG. 5c, the shape of the recess 214 is independent from the shape of the insertion tool (but the recess will conform to the restraint later inserted).

Figures 6A, 6B:
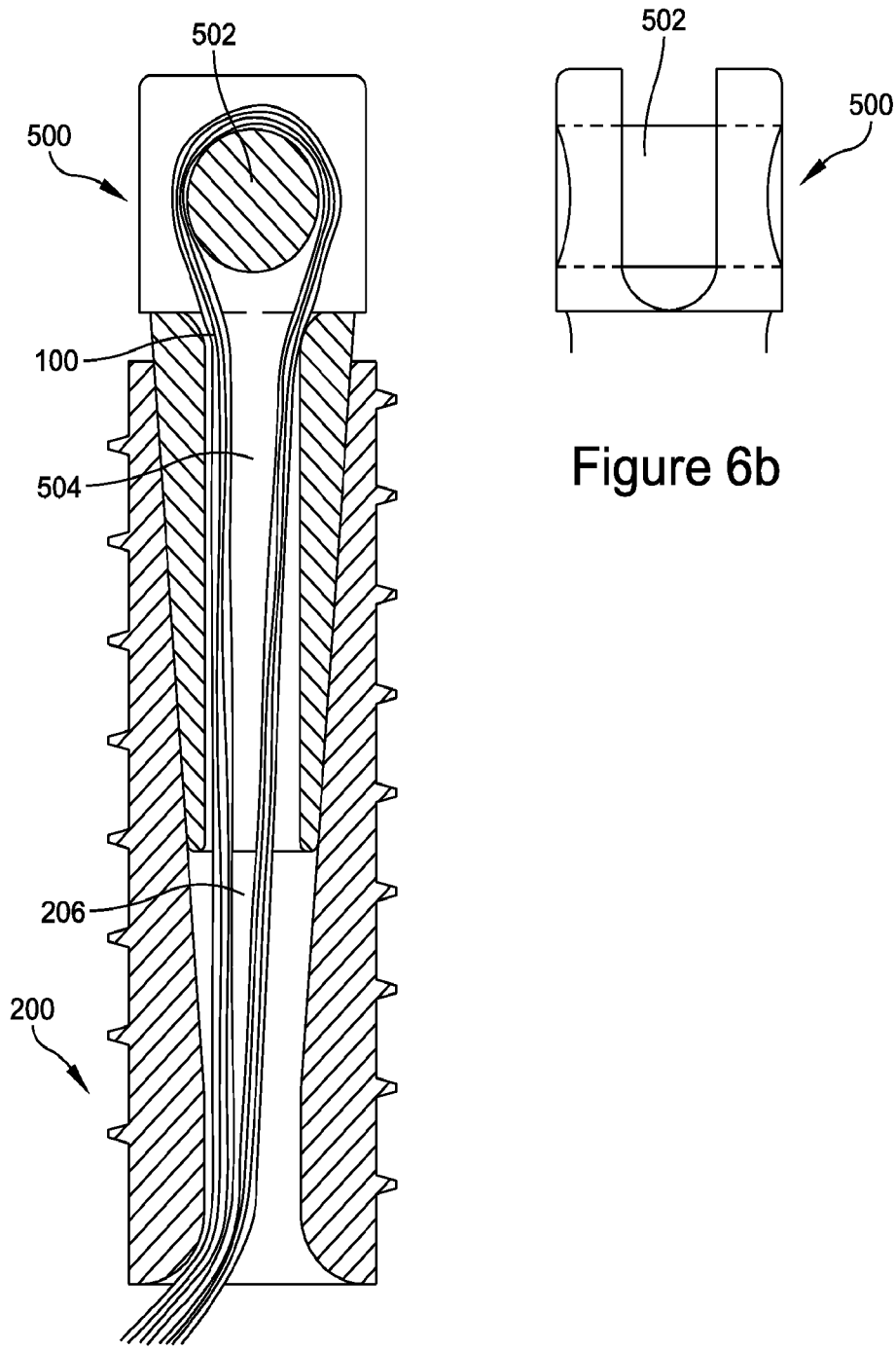
FIG. 6 shows a separable restraint with a transverse pin and internal longitudinal channel.

Referring to FIG. 6, a separable restraint 500 is illustrated that bears the prosthetic ligament 100 around a transverse cylindrical element 502 or "pin". The prosthetic ligament 100 travels from the pin 502 through a single internal longitudinal channel 504 that is contiguous with the longitudinal tunnel 206 of the anchor 200 (FIG. 6a). An orthogonal view of the transverse pin 502 running through the separable restraint 500 is shown in FIG. 6b. The transverse cylindrical element 502 may be removable from the separable restraint 500 in order to position the prosthetic ligament 100 or it may be integral with the separable restraint 500.

Referring to FIG. 7, a separable restraint 600 is illustrated having a non-axial internal channel 602 (FIG. 7a). Rounded channel entry 604 is shown at the proximal end of the restraint 600, having a radius of curvature to reduce stress on the prosthetic ligament. A curvilinear pathway 606 is defined including the linear internal channel through the dowel. At no point along the pathway of the ligament does the line defining the ligament path curve with a low radius of curvature. In some embodiments, the lowest radius of curvature along this pathway is equal to one-half of the radius of curvature of the curved exit 210. The pathway places one end of the prosthetic ligament across a saddle shaped end 608 of the restraint 600 as the other end of the ligament loop is directed into the internal channel 602 of the restraint. A hook of smooth and continuous geometry is represented. The sides of the pathway in the restraint are curved to centralize the ligament in the defined pathway, and to inhibit lateral movement on the pathway associated with tension on the ligament. The pathway is preferably deep enough to prevent escape from the saddle area if there is laxity on the ligament, and one embodiment includes depth sufficient to allow parallel sides of the pathway. The surface of the ligament pathway can be made smooth and abrasion resistant in much the same way as the curved exit 210 surface to prevent damage to the ligament. The longitudinal channel may be placed in a non-coaxial position to allow more space for the saddle hooks 610 and to facilitate the fabrication process.

FIG. 7b illustrates an anchor in which the restraint is integrated with the body of the anchor 650. The geometry of the restraint pathway and saddle configuration is much the same as in FIG. 7a. The longitudinal tunnel 652 may be non-coaxial with the anchor 650, much as with the longitudinal channel in FIG. 7a. It may be preferable to allow placement of the prosthetic ligament after countersinking of the anchor so the saddle opening 654 lies within the hole that has been drilled for the anchor 650. Alternatively, if the anchor is designed to reside with the trailing end projecting from the bone, then the radius on a portion of the trailing end may exceed the radius of the drilled hole, and a larger saddle, which may be more easily mounted, may be included.

Figure 8:
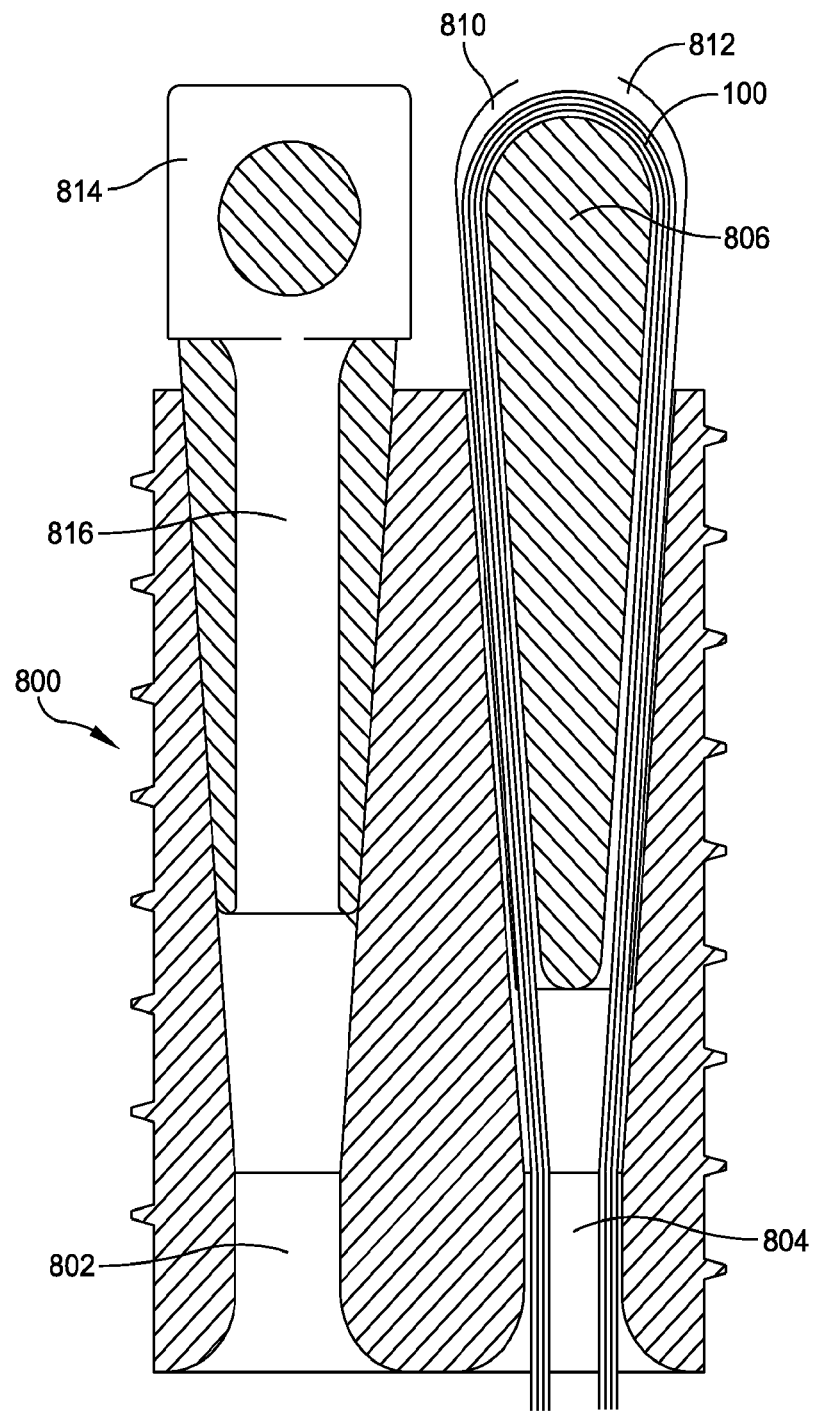
FIG. 8 shows a dual-lumen anchor, a separable restraint with external channels, and a separable restraint with an internal channel.

Referring to FIG. 8, a dual-lumen anchor 800 is illustrated. The spacing of the two longitudinal tunnels 802 and 804 can correspond to the anatomic spacing of the anteromedial and posterolateral bundles of the anterior/cranial cruciate ligament. This dual lumen anchor allows placement of double bundle ligament reconstruction with drilling only one hole. A double-bundle reconstruction could also be achieved in the context of the present invention by placing two pairs of single-lumen anchors in the appropriate positions. Also shown in FIG. 8 is a representation of a prosthetic ligament 100 looped over a separable restraint dowel 806, which can be the same as or similar to that shown in FIG. 3f as item 300. A longitudinal cross section through the external longitudinal channels 810 and 812 is shown. The saddle geometry of the trailing end of the separable restraint is substantially the same as the geometry of the ligament path restraint geometry in FIGS. 7a and 7b. Also shown is a separable restraint dowel 814 that has an internal channel 816, as previously shown in FIG. 6.

Figure 9:
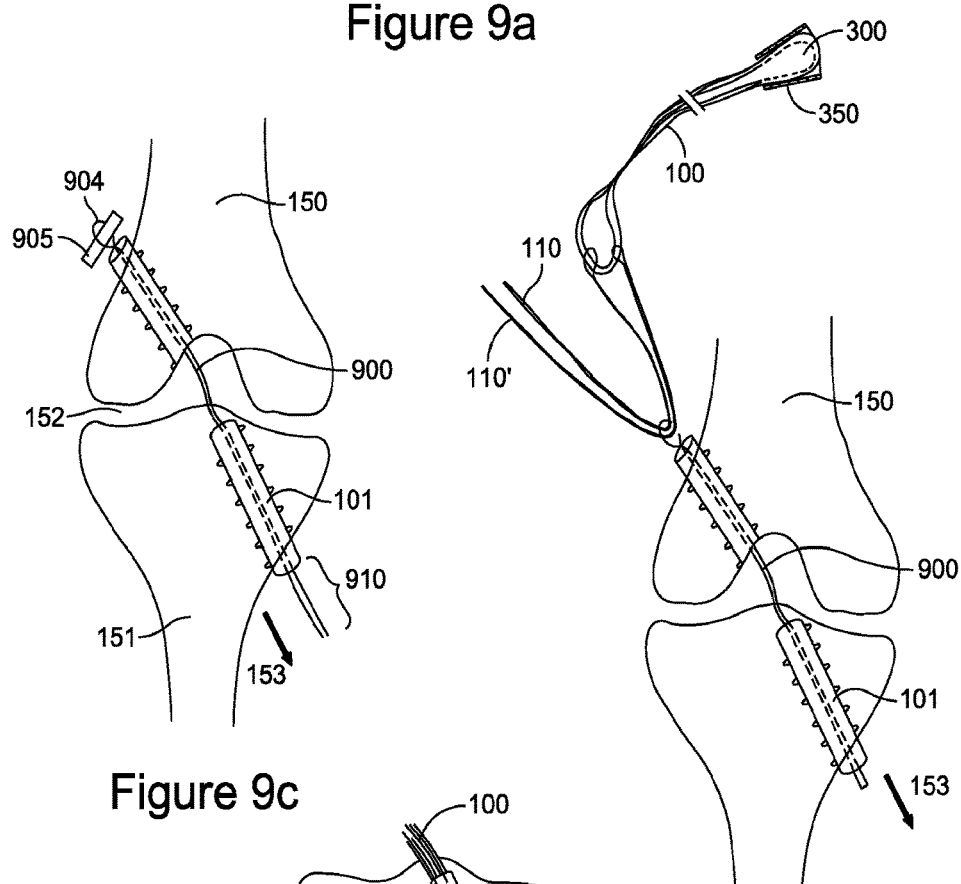
FIG. 9 shows a threader and illustrates insertion of a prosthetic ligament at the knee joint.

Referring to FIG. 9, the present prosthetic system can also include a prosthetic ligament loop threader 900, which we may refer to more simply as the threader (FIG. 9a). A shaft 902 can be formed by welding a length of filament (e.g., polymeric filament), leaving an open loop 904 at one end. The weld at plane C-C is illustrated in cross-section in FIG. 9b. In addition to facilitating the insertion of the prosthetic ligament through the first and/or second anchors, the threader can assist in the selection of a prosthetic ligament of an accurate length. More specifically, the threader can include markings reflective of length. As described further below, by inserting the threader through the first anchor, across the intraarticular space (e.g., when the joint is extended), and through the second anchor, the surgeon will be able to estimate the length of the prosthetic ligament that is needed based on the measurement provided by the markings on the threader (and fine adjustments can be made after the ligament is placed).

We have selected, the knee joint to further illustrate insertion and fixation of the prosthetic ligament. Methods including the steps of inserting and/or fixing the present prosthetic ligament within a subject (e.g., a human patient or non-human mammal) are within the scope of the present invention.

Insertion of the anchors 200 and 101 into the femur 150 and tibia 151 is done from outside in with the aid of a drill guide so that the leading end of the anchor 200 enters the joint space 152 at the approximate anatomic origin of the ACL and the leading end of the tibial anchor 101 enters the joint space 152 at the approximate insertion of the ACL (FIG. 9c). The threader 900 provides an approximate measure of the required length of the prosthetic ligament, which is equal to the length of the threader 900 minus the length 910 of the threader extending beyond the trailing end of the tibial anchor 101 when the threader loop 904 is pulled tight against a threader stop 905 when the joint is in extension (FIG. 9c). The direction of the threader is indicated by arrow 153.

After the required measurement is obtained, the threader is then used to pull the passing leads 110 and 110' of the measured/selected prosthetic ligament 100 through the anchor 200, the joint space 152 and the tibial anchor 201 as shown by arrow 153 in FIG. 9d. The prosthetic ligament 100 can be a part of an assembled prosthetic ligament, including a separable restraint 300 that comes to rest in the recess of the trailing end of the anchor 200. The threader 900 pulls the passing leads 110 and 110' through the anchors 200 and 201. Traction on the passing leads then pulls the prosthetic ligament through. According to proper measurement of the prosthetic ligament 100 with the threader, the ligament extends a short distance beyond the trailing end of the tibial anchor 201. The passing leads 110 and 110' are then used to spread open the end 115 of the prosthetic ligament 100, which is secured with a second restraint 310 (FIG. 9e). Alternatively, a non-looped ligament may be selected by the surgeon, and after passing and proper tensioning of the ligament, the free ends may be connected over a restraint by tying or other means.

To secure the prosthetic ligament with a second restraint 310, an ear 365 of a terminal dowel sheath 360 is passed through the opening generated when the passing leads are pulled in two directions 154 and 155. The terminal restraint 310 can then be placed in the conical recess of the trailing end of the tibial anchor 101. The terminal restraint 310 can be optionally fitted with a sleeve and the loop 303 of the prosthetic ligament 100 fitted into the groove 302 of the restraint 360. This can be done with the joint in flexion where the length of the ACL is several millimeters shorter than when the joint is in extension. Once the terminal restraint 310 is in place, the joint is extended tightening the prosthetic ligament loop 100. In order to fine tune the length of the prosthetic ligament within the joint space 152, several terminal dowels of different lengths can be provided (e.g., in a kit comprising components of the prosthetic system of the invention).

Handling of the terminal restraint 310 in surgery is facilitated by the dowel sheath 360, which is removed after it has served its purpose. The surgeon would peel the sheath 360 apart by pulling on the dowel sheath ears 365 and discarding the sheath 360.

The terminal restraint 310 can be inserted into the conical recess of the tibial anchor 101 prior to feeding the prosthetic ligament loop threader 900 through the anchor screw 101. Interposing a dowel sleeve between the terminal dowel 310 and the screw anchor 101 protects the filaments of the loop 100. Alternatively, insertion of the ligament may be from the tibial side toward the femoral side, inverting the procedure as outlined above.

The Anchor: In the prosthetic systems described herein, the curved exit from the longitudinal tunnel of an anchor has a radius of curvature, as described herein, and preferably provides a hard surface along which the ligament prosthesis is guided as it exits the anchor and enters the intra-articular space. The shape and content of the exit can be provided by an eyelet within the anchor or by the anchor per se. For example, a ceramic material can be integrated with the body (e.g., as a surface coating) rather than provided as a separate piece (i.e., the eyelet) that is joined to the body of the anchor. Constructing an anchor body from a hard material such as ceramic allows the anchor to better tolerate ligament contact and abrasion. The anchor can be solid ceramic. As noted, tolerance can also be provided by a suitably hard and well-shaped eyelet. Many hard surfaces can be employed, and these include ion implanted, cermet (Spire Corporation), ADLC (Ion Bon, Inc.), and nitrided surfaces.

Cobalt Chrome alloys such as MP35N®, L-605®, and ASTM-F1058 are strong, hard, and corrosion resistant. These qualities, in combination with excellent biocompatibility, make these alloys ideal for long-term joint replacement implants and fracture repair, and each options for fabricating the present implants. The anchors are preferably made from titanium or a titanium alloy (e.g., TiAl6V4 or TiAl6Nb7). In one embodiment, the rounded exit from the axial tunnel has a low surface roughness, and may be polished, and may have a surface hardening treatment, and among such treatments it may be coated by a hard, low friction coating (e.g., an amorphous diamond-like coating (ADLC), or other coatings). The curved exit of the anchors can be of a radius of about 1 to 1.5 mm.

Figure 10:
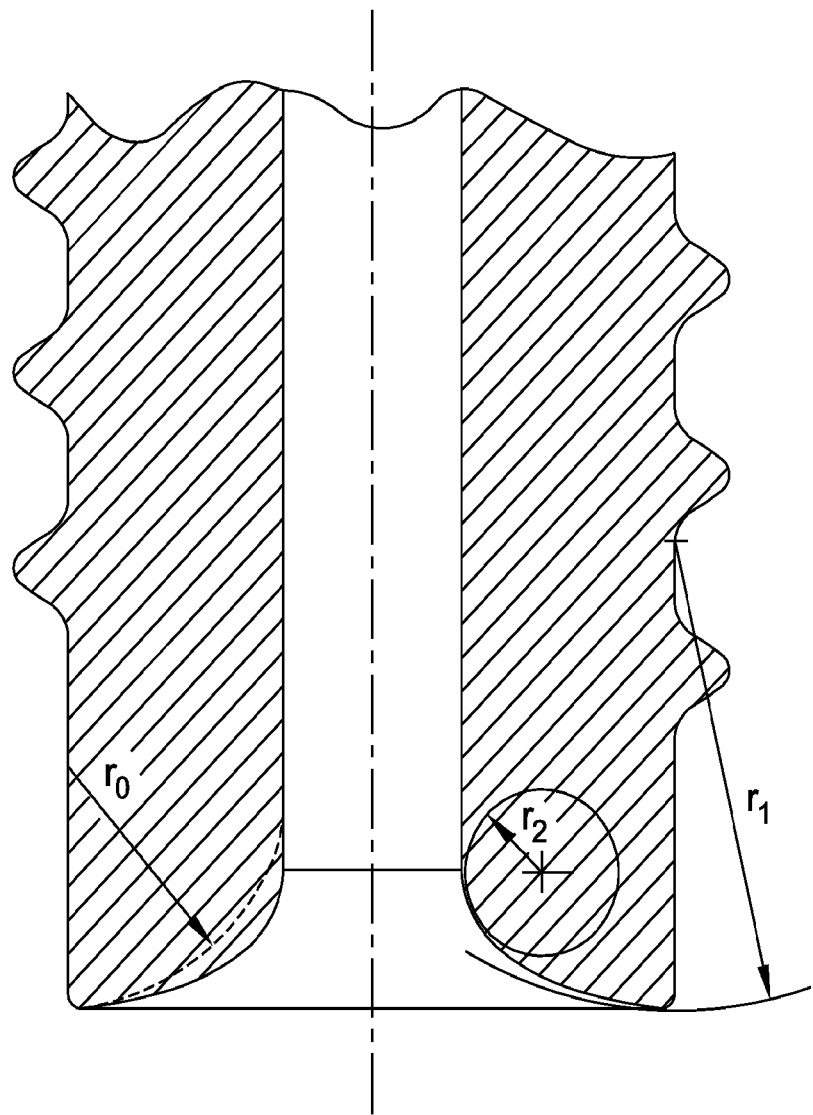
FIG. 10 illustrates that the radius of curvature can increase progressively toward the exit of an anchor.

Alternatively, the radius can increase from a small radius at the tunnel (e.g., about 0.5 mm) to a larger radius (or progressively larger radii) toward the exit of the anchor; the radius of curvature can increase progressively toward the exit of the anchor (FIG. 10). As illustrated in FIG. 10, instead of making the maximum allowed radius r0, limited by the dimensions of the anchor, one can vary the radius from a smaller one, r2, at the tunnel, to a larger one, r1, at the very exit from the anchor. Since the fibers wrap around about 90 degrees over the curve, the so-called "capstan equation" suggests that the force on the fiber in the tunnel is reduced by about 20% if the coefficient of friction is 0.15 (which is typical of UHMWPE, on hard surfaces). There may, therefore, be an advantage to making the radius at the exit larger and thereby reducing the bending component of the stress on the fiber, and then gradually decreasing the radius of curvature on the way to the inside of the tunnel.

If the fiber of diameter d is bent around a cylinder of diameter D, the strain induced in the fiber is epsilon=d/D. If the fatigue limit for the fiber is epsilon-max ($\varepsilon_{max}$) then just flexing the fiber around the cylinder of diameter D=d/$\varepsilon_{max}$ will break the fiber (at the number of cycles at which the $\varepsilon_{max}$ has been established). Just bending the fiber can result in failure. To function usefully, the fiber needs not only to bend, but also to resist some tension as well. This indicates a larger cylinder in order to leave some capacity for tension. We have defined this larger diameter by making it a factor "k" larger. That is, D=k(d/$\varepsilon_{max}$). Now, the bending strain around this cylinder is epsilon=$\varepsilon_{max}$/k, or "k" times lower. Concerning the remainder for tension, epsilontension=e $\varepsilon_{max}$-$\varepsilon_{max}$/k=$\varepsilon_{max}$, (k-1)/k. If we choose k=2, epsilontension=(½) $\varepsilon_{max}$, i.e. one half of the fiber capacity is used up by bending and one half to resist tension. If k=3, then ⅔ of the capacity is used for tension and ⅓ for bending. The balance is given by affordable geometry/dimensions of the anchor. While in principle larger radii are preferable, there are anatomical constraints. Thus, choosing k-2 (for a 50/50 compromise) demands D=2*d/$\varepsilon_{max}$. For d=0.010 mm (which is a size described for suitable fibers herein) and $\varepsilon_{max}$=0.015, we need D=2*0.01/0.015=1.33 mm, or the radius=D/2=0.67 mm. This is just one possible compromise. With a radius of 1 mm, one arrives at k=2*0.015/0.01=3. That is, ⅔ of the fiber capacity will be used towards functional tension. Larger "k" values are possible where there is adequate space. Ultimately, this is decided by the anatomy of the joint.

In one embodiment of the invention, the anchors include a separate eyelet at an exit from the longitudinal tunnel. The eyelet can be made from a ceramic providing a smooth, hard surface for the radius, or the eyelet may have a ceramic coating. In another embodiment, the eyelet is made of ruby or sapphire.

Whether provided by the body of the anchor or an eyelet therein, the arc at the exit can be at least or about 80-90° (so the range of motion on the femoral side falls within the 2×(80-90°) arc).

Further regarding the radius of curvature R at the exit eyelet, it has been shown that the strain ε experienced at the surface of a fiber bent to this radius of curvature R is equal to d/2R. If the maximum allowable strain avoiding fatigue failure of the polymer is $\varepsilon_{max}$, then the minimum allowable radius of curvature over which the fiber may be cyclically bent is d/2 $\varepsilon_{max}$. Adding a factor for maximum strain associated with tension on the ligament, the invention considers a tensile strain up to the strain associated with bending over radius R. Both of these strains applied simultaneously reduce the allowable strain contribution from bending, and therefore R is increased by a factor k. This factor k is about or greater than one, and is optimized in this invention not to exceed four (e.g., k can be about 1, 2, or 3). This is based on the optimization of having the strain from tensile loading not exceed the strain from bending. Hence the optimal radius of curvature of the exit is greater than to Kd/2 $\varepsilon_{max}$, where the exact value for K is determined by chosen excessive design strength for tensile loading.

Additionally, this invention includes the systematic determination of anchor minimum diameter D, according to the ligament polymer used, the fiber diameter d, and the anticipated cyclic tensile force T in the ligament. In this case, the design is optimized to have equal cyclic strain contributions from fiber bending and tensile loading, eliminating the factor k.

$$D = 2d/\varepsilon_{max} + \frac{4\sqrt{T*\sqrt{3}}}{\pi\sqrt{E\varepsilon_{max}}}$$

The arc of curvature of the exit hole is chosen to accommodate the full range of motion of the knee such that the ligament remains in contact with the leading end with only the surface having a radius R. In general the arc on each side of the hole is 90 degrees, but for application in the femoral side of the knee, there may be circumstances that require continuing the arc to greater than 100 degrees. This is especially true if the anchor is placed at an angle such that in full knee extension, the angle between the ligament and the anchor axis is greater than 90 degrees.

In cross-section, the anchor is of a generally cylindrical shape, having an axis and having an outer thread. There is generally a significant difference between the longitudinal hole and the outside diameter, and this relationship is another part of a new approach to ligament reconstruction. When an anchor has a thin wall, the only way to increase the radius of curvature of the exit is to place a flange on the intra-articular end of the anchor, the flange having a greater diameter than the anchor body. However, the present anchors are more thick-walled, allowing a greater radius of curvature at the exit without using a flange of larger diameter. A flange at the leading end of the anchor prevents outside-in insertion of the anchor on the femoral side, and prevents all placement on the tibial side. The ratio between the outside diameter of the anchor and the diameter of the exit hole at its smallest point (before curving outward and exiting the anchor at the leading end) may be at least or about 2:1 (e.g., 3:1, 3.5:1 or 4:1).

As noted, another feature of the present invention is that the prosthetic ligament can be much smaller than the anatomic ligament that it is replacing. This feature allows the prosthetic ligament to originate from an area much smaller than the anatomic ligament. A large cross-section ligament reconstruction does not duplicate the optimal isometric point of the original anatomic ligament. The development of a small cross-section ligament for reconstruction allows the surgeon to more nearly duplicate the optimal isometric point for placement of the ligament.

Another feature of the present invention is that the outer diameter of the anchor can be much greater than is necessary for the prosthetic ligament. The prosthetic ligament material is exceptionally strong, and surrounding it with a very narrow anchor would not present sufficient surface area to the soft cancellous bone in the locations adjacent to the joints. By developing a much thicker anchor body than is needed to pass the ligament, adequate surface area for load transfer on the outer surface of the anchor is achieved.

Insertion Tool. As noted, the prosthetic system described herein can be deployed with the aid of an insertion tool that is adapted to the anchor and any special needs of the associated surgical operation. One such tool is shaped to engage an external surface of the trailing end of the anchor. For example, the insertion tool can engage an irregularity (e.g., an indentation or angular face) on an external surface of the trailing end of the anchor. The irregularity can be within the major diameter of the anchor's elongated body or within the major diameter of any threads extending from the elongated body. Another such tool is shaped to engage an internal surface of the trailing end of the anchor. For example, the insertion tool can engage an internal cannulation or recess.

An insertion tool and its cognate anchor can have conical or non-conical engagement geometry, and in either event, the cannula or recess that receives the insertion tool can be circular or non-circular in cross-section. Thus, the internal cannula or recess can be conical and circular in cross-section; conical and non-circular in cross-section; non-conical and circular in cross-section; or non-conical and non-circular in cross-section. Whether tapered or non-tapered, where an internal cannula or recess is non-circular in cross-section, it may be polygonal (e.g., a triangle, pentagon, hexagon, or octagon). We may also describe a conical cannula or recess as tapered. Non-tapered areas of engagement are essentially constant in cross-section (transverse section).

The area of engagement between the tool and the anchor may be greater than one-half the radius of the anchor, as measured along the axis of the tool and the anchor. This degree of engagement provides improved axial stability of the anchor with respect to the tool and improved directional control of the anchor during the insertion process.

The insertion tool itself can be cannulated. This allows a surgeon to insert the threader immediately after anchor insertion, with the insertion tool still in place; a cannulated insertion tool need not be removed prior to working with the threader.

The cannula or recess in the trailing end of the anchor can be multi-functional. In one embodiment, the same recess can receive an insertion tool at a first point in time and a separable restraint at a second point in time. For example, the trailing end of the anchor can include a conical recess that is designed to engage a tapered insertion tool as well as a similarly tapered restraint. As noted, the recess can be circular or non-circular in cross-section and, notably, torque can be effectively transferred through a tapered recess that is circular in cross-section. In another embodiment, different portions of the cannula or recess in the trailing end can receive the insertion tool and the separable restraint. Thus, the cannula or recess may have separate surfaces of engagement for the insertion tool and the separable restraint. For example, the two surfaces may have different geometries (e.g., conical and prismatic).

Integral Restraints and Supplemental or Separable Restraints. Where a restraint is an integral part of an anchor, it can be made of the same materials from which the anchor was made. Any of the separable restraints described herein can also be made from the same materials from which the anchors are made. For example, a restraint can be made from titanium or a titanium alloy (e.g. TiAl6V4 or TiAl6Nb7), and optionally coated by a low friction, hard coating (e.g. ADLC). One form of a separable restraint is the dowel or plug as described herein, which may restrain and guide the prosthetic ligament through the prosthesis by a pair of longitudinal channels running along its external surface or a single longitudinal channel running through an internal surface. An advantage of the centrally located channel is that a dowel sleeve may be unnecessary. Where a dowel sleeve is used, it can be made from PEEK tubing or from some other polymer tubing or material that may or may not be heated to encapsulate the dowels.

Ligament Prostheses: The fibers or filaments (which we may refer to as "monofilaments") of the ligament prosthesis can have a small diameter in order to limit the bending strain associated with bending over a given radius of curvature, and multiple fibers or filaments can operate together to provide the necessary strength for the prosthesis. Unless the context clearly indicates otherwise, we use the terms "fiber(s)" and "filament(s)" or "monofilament(s)" interchangeably. "Yarn" refers to a group of fibers as they are usually supplied by a vendor (as it is generally not practical to handle single monofilaments in the size range of 10-20 microns). The fibers may be independent in the sense that they are not braided, bonded, twisted, or otherwise entangled, other than as supplied as a yarn. However, as noted, intermingled fibers (as in yarns) can be further engaged. For example, the yarns may be intermingled by braiding, twisting, or other integration (for example, according to the preference of the surgeon).

One possible disadvantage of intermingled fibers is that they may be more susceptible to infection (our view on this is evolving). For example, bacteria within a braided ligament prosthesis may not be as accessible to immune system cells. To further increase resistance to infection (which may be preferable in any circumstance where surgical conditions are less than ideal), some or all of the fibers within the ligament prosthesis can be prepared with a content of silver or another antibacterial agent.

All or a portion of the multifilament, ligament prostheses can be held together with a gelatin or other substance, or contained by a surface-covering (e.g., surface-wrapping) fiber, that will dissolve within the body. The addition of a temporary binding agent may make the prosthesis easier to use, yet allow the filaments to separate later in order to achieve improved wear and failure resistance.

In any of the embodiments described herein, the ligament prosthesis can be fashioned from material(s) that are not bio-absorbable. As noted, the ligament prosthesis can be formed of a plurality of filaments or fibers. Such filaments or fibers may include oriented, high modulus, ultra high molecular weight polyethylene (UHMWPE). Filaments or fibers of UHMWPE are commercially available from manufacturers such as DSM (in the Netherlands; selling under the trademark DYNEEMA®) and Honeywell (in the USA; selling under the trademark SPECTRA®). Preferably, the diameter of the fiber (i.e., an individual monofilament) is between about 10 and 20 micrometers (e.g., about 15 micrometers). The fibers are free from each other (i.e. no diffusion bonding or braiding is used in production). The ends may be fused, preferably with an aid of low molecular weight polyethylene, to facilitate tying of the knots and insertion through the anchors. Other suitable polymeric fibers are polyethylene teraphthalate (polyester), polyamide (NYLON®), aramid (KEVLAR®), and silk. The fibers useful in the present prosthetic ligaments can be gel-spun, highly-oriented, high-strength, high-modulus fibers, including, as noted, UHMWPE fibers. Suitable molecular weights are in the range of 2 to 6 mio Dalton, and high strength includes more than 3 GPa.

Double-Bundle Ligaments. As noted, the elongated body of an anchor can define a pair of longitudinal tunnels that accommodate a "double-bundle" ligament. As some natural ligaments twist as the joint moves in certain ways, the double-bundle ligament may more closely mimic natural events. We may refer to anchors having a defined pair of longitudinal tunnels as having a dual lumen. As with single lumen anchors, each longitudinal tunnel or lumen can terminate at the lending end of the anchor in a curved exit. As with single lumen anchors, the curved exit can be integral to the body of the anchor or provided by a distinct eyelet. Thus, anchors having dual lumens can have double eyelets with any or all of the same properties or characteristics described herein for anchors with a single longitudinal tunnel.

Threader. The prosthetic systems described herein can be deployed with the assistance of a threader, which we may also refer to more fully as a prosthetic ligament loop threader. The materials used to make the threader can be metallic or polymeric so long as they can produce a threader that is sufficiently stiff to pass through the cannulated anchor yet flexible enough to negotiate any required change in direction through the joint.

Considered as a whole, the prosthetic system described herein can include any combination (including all) of the following features: a fiber material such as oriented UHMWPE, a curved exit including a radius of curvature with a particular relationship to the diameter of the fibers in the prosthetic ligament, a material at the curved exit that provides a certain degree of smoothness, bone-to-anchor contact material, and surface area.

Methods of Use: The prosthetic systems described herein can be used to treat a variety of patients (i.e., the systems have human clinical application as well as veterinary application) and a variety of joints within a patient. The same principles of design and deployment can be used to repair, for example, the joint at the shoulder, elbow, wrist, hip, knee, or ankle. A particular use is in the repair of the so-called round ligament in the hip joint, frequently ruptured by trauma in dogs.

As noted above, a surgeon may select a ligament prosthesis with either independent or intermingled fibers. When the fibers are tightly integrated they will experience greater individual stress and be less resistant to individual failure. In some circumstances, the surgeon will prefer gradual attrition of the fibers, as this allows natural body tissues to assume the load. This parameter can be adjusted by adjusting the density of the ligament prosthesis and the type of fiber integration. Surgeons may also adjust the tension of the prosthetic ligament in different ways. For example, the surgeon could adjust the tension by coupling the ligament loop at different lengths, or adjusting the length of the loop. Selecting a non-looped ligament prosthesis in which the fibers are intermingled (e.g., as a cord) or bound together allows the surgeon to adjust a given ligament prosthesis to a desired length, because the fibers are simply more amenable to manipulation. The degree of fiber integration can be adjusted from essentially no integration (i.e., substantially parallel fibers), to tight integration (e.g., as is seen with typical cordage), with the degree of integration varying according to surgeon preference and intended use. Our systems feature the use of intermingled fibers as an alternative means to equalize partially the tension in individual fibers, as the tighter fibers assume a more nearly straight orientation, causing more bending and more tension in those fibers originally having less tension.

An additional advantage of the present system is that a surgeon can replace the prosthetic ligament if failure occurs sometime after the surgery without replacing the anchors. This surgery is much more straightforward than replacing a failed autograft or allograft ligaments.

In positioning an anchor of the present system, a surgeon can employ a target guide wire with a tenaculum clamp to define both an entry hole and an exit hole, with the guide parallel to the points of the tenculum. Guide wires can be advanced inside-out or outside-in, and a cannulated drill is used to generate bone holes placed according to placement of the guide wires (as is known in the art).

Having disclosed at least one embodiment of the present invention, variations will be understood by one of ordinary skill in the art. Such adaptations, modifications, additions and improvements are considered part of the invention.

What is claimed is:

1. A prosthetic system for surgical repair of a joint, the system comprising a first anchor, a second anchor, a prosthetic ligament, a first separable restraint, and a second separable restraint, wherein:

the first anchor comprises an elongated body defining a longitudinal tunnel that connects a leading end of the first anchor with a trailing end of the first anchor;

the second anchor comprises an elongated body defining a longitudinal tunnel that connects a leading end of the second anchor with a trailing end of the second anchor, wherein the first anchor and the second anchor are insertable into bones;

the first separable restraint is received in a first receiving surface of the trailing end of the first anchor, the first separable restraint defining a first restraint tunnel;

the second separable restraint is received in a second receiving surface of the second anchor, the second separable restraint defining a second restraint tunnel; and the prosthetic ligament comprises a plurality of fibers of non-natural polymer that form contiguous loops and the prosthetic system is configured such that, when the system is deployed, a first end of the plurality of fibers is held by the first restraint at the trailing end of the first anchor and a second end of the plurality of fibers is held by the second restraint at the trailing end of the second anchor, such that a first portion of the prosthesis lies within the longitudinal tunnel that connects the leading end of the first anchor with the trailing end of the first anchor and a second portion of the prosthesis lies within the longitudinal tunnel that connects the leading end of the second anchor with the trailing end of the second anchor, wherein the longitudinal tunnel of the first anchor is contiguous with the first restraint tunnel and the longitudinal tunnel of the second anchor is contiguous with the second restraint tunnel;

wherein at least one of a first pathway formed by the longitudinal tunnel of the first anchor and the first restraint tunnel or a second pathway formed by the longitudinal tunnel of the second anchor and the second restraint tunnel, defines a curvilinear pathway with a radius of curvature that is at least one half of an exit radius of a respective at least one of curved exits of the longitudinal tunnel of the first anchor or the longitudinal tunnel of the second anchor, the curvilinear pathway being a curved line defining a ligament path curved inside the first pathway or the second pathway through which the prosthetic ligament passes, wherein the leading end of the first anchor or the second anchor comprises a curved exit and wherein the curved exit is integral to the leading end of the first anchor or the second anchor or is formed by means of including an eyelet surrounding the longitudinal tunnel at the leading end of the first anchor or the second anchor.

2. The prosthetic system of claim 1, wherein the elongated body of the first anchor or the second anchor comprises an outer surface at least partially covered by threads.

3. The prosthetic system of claim 1, wherein a portion of the trailing end of the first restraint or the second restraint is shaped to engage an insertion tool.

4. The prosthetic system of claim 1, wherein the restraint is an integral part of the trailing end of the first anchor.

5. The prosthetic system of claim 1, wherein the curved exit has a surface with a roughness, $R_a$, less than about 0.5 µm.

6. The prosthetic system of claim 1, wherein the curved exit has a surface comprising a ceramic.

7. The prosthetic system of claim 1, wherein the curved exit has a surface that is ion implanted, diffusion hardened, oxidized, or treated using an ion beam assisted deposition process.

8. The prosthetic system of claim 1, wherein the curved exit has a surface comprising an oxidized metal.

9. The prosthetic system of claim 1, wherein the curved exit has a radius of curvature of at least $(k/2)(d/\varepsilon_{max})$, wherein d is the diameter of individual fibers in the prosthetic ligament, $\varepsilon_{max}$ is the allowed strain in fatigue of the fibers' material, and k is a factor between 1 and 4 allowing for strain associated with suture tension in cyclic use.

10. The prosthetic system of claim 1, further comprising a passing lead, wherein the passing lead is secured around the prosthetic ligament and configured to facilitate passage of the prosthetic ligament from the leading end of the first anchor, across the gap between the first anchor and the second anchor, and through the second anchor.

11. The prosthetic system of claim 10, wherein the system comprises a pair of passing leads.

12. The prosthetic system of claim 1, wherein the elongated body defines a pair of longitudinal tunnels that connect a leading end of the first anchor with a trailing end of the first anchor.

13. A method of surgically repairing a joint, the method comprising deploying the prosthetic system of claim 1 in a patient in need of treatment.

14. The method of claim 13, wherein the method comprises the steps of:
 (a) providing a bone hole in each of two opposing bones,
 (b) placing, in each bone hole, an anchor, and
 (c) passing the prosthetic ligament (i) through a first anchor, from the trailing end of the first anchor to the leading end of the first anchor, (ii) across the gap between the two opposing bones, and (iii) through the second anchor, from the leading end of the second anchor to the trailing end of the second anchor.

15. The prosthetic system of claim 1, wherein the fibers are present as individual fibers that are monofilaments or the fibers are present in groups such as in the form of a yarn.

16. The prosthetic system of claim 15, wherein the fibers are intermingled and wherein the intermingled fibers are braided, twisted, or braided and twisted.

17. The prosthetic system of claim 15, wherein the fibers have diameters in the range of about 10 to 20 µm.

18. The prosthetic system of claim 15, wherein the fibers are formed from a high strength, high modulus polymer.

19. The prosthetic system of claim 18, wherein the high strength, high modulus polymer comprises polyethylene.

20. The prosthetic system of claim 1, wherein the first restraint tunnel and the second restraint tunnel are non-axial relative to the longitudinal tunnel of the first anchor and the longitudinal tunnel of the second anchor, respectively.

21. The prosthetic system of claim 1, wherein the first restraint tunnel and the second restraint tunnel define a first and second curvilinear pathways, wherein a radius of curvature of the first and second curvilinear pathways is at least one half of exit radii of curvature for curved exits of the longitudinal tunnel of the first anchor or the longitudinal tunnel of the second anchor.

22. The prosthetic system of claim 1, wherein the elongated body of the first anchor has a first anchor diameter, the elongated body of the second anchor has a second anchor diameter, the longitudinal tunnel of the first anchor has a first minimum tunnel diameter, and the longitudinal tunnel of the second anchor has a second minimum tunnel diameter, and wherein the ratio of the first anchor diameter to the first minimum tunnel diameter is at least 2:1, and the ratio of the second anchor diameter to the second minimum tunnel diameter is at least 2:1.

\* \* \* \* \*